United States Patent
Sakai et al.

(10) Patent No.: US 9,078,834 B2
(45) Date of Patent: Jul. 14, 2015

(54) HAIR COSMETIC

(75) Inventors: Atsushi Sakai, Tokyo (JP); Kouji Morita, Tokyo (JP); Youko Nobuhara, Tokyo (JP)

(73) Assignee: KAO CORPORATION, Tokyo (JP)

( * ) Notice: Subject to any disclaimer, the term of this patent is extended or adjusted under 35 U.S.C. 154(b) by 39 days.

(21) Appl. No.: 13/809,015

(22) PCT Filed: Jul. 5, 2011

(86) PCT No.: PCT/JP2011/003833
§ 371 (c)(1),
(2), (4) Date: Jan. 8, 2013

(87) PCT Pub. No.: WO2012/004981
PCT Pub. Date: Jan. 12, 2012

(65) Prior Publication Data
US 2013/0104923 A1    May 2, 2013

(30) Foreign Application Priority Data

Jul. 8, 2010 (JP) .................................. 2010-156198

(51) Int. Cl.
*A61Q 5/00* (2006.01)
*A61Q 5/12* (2006.01)
*A61K 8/81* (2006.01)
*A61K 8/88* (2006.01)
*A61K 8/34* (2006.01)
*A61K 8/41* (2006.01)
*A61K 8/42* (2006.01)

(52) U.S. Cl.
CPC .............. *A61K 8/8164* (2013.01); *A61K 8/342* (2013.01); *A61K 8/41* (2013.01); *A61K 8/42* (2013.01); *A61K 8/8194* (2013.01); *A61K 8/88* (2013.01); *A61Q 5/00* (2013.01); *A61Q 5/12* (2013.01)

(58) Field of Classification Search
None
See application file for complete search history.

(56) References Cited

U.S. PATENT DOCUMENTS

| 6,069,216 | A | 5/2000 | Iwasaki et al. |
| 7,960,327 | B2 * | 6/2011 | Uchiyama et al. ............ 510/130 |
| 2006/0078527 | A1 | 4/2006 | Midha et al. |
| 2006/0251602 | A1 | 11/2006 | Goddinger et al. |
| 2007/0166272 | A1 | 7/2007 | Kaharu |
| 2008/0138307 | A1 | 6/2008 | Bazemore et al. |
| 2010/0284956 | A1 | 11/2010 | Hayashi et al. |

FOREIGN PATENT DOCUMENTS

| CN | 100998548 | A |  | 7/2007 |
| CN | 101111286 | A |  | 1/2008 |
| CN | 101415401 | A |  | 4/2009 |
| JP | 6 48916 |  |  | 2/1994 |
| JP | H11-071435 | A1 |  | 3/1999 |
| JP | 2003 327513 |  |  | 11/2003 |
| JP | 2004 67534 |  |  | 3/2004 |
| JP | 2006 517937 |  |  | 8/2006 |
| JP | 2008 515921 |  |  | 5/2008 |
| JP | 2008 528541 |  |  | 7/2008 |
| JP | 2008-184424 |  |  | 8/2008 |
| JP | 2009 173586 |  |  | 8/2009 |
| WO | WO 2006/042180 | A1 |  | 4/2006 |
| WO | WO 2008/004342 |  | * | 1/2008 |
| WO | WO 2009/084217 |  | * | 7/2009 |
| WO | WO 2009/084217 | A1 |  | 7/2009 |

OTHER PUBLICATIONS

Written Opinon of the International Searching Authority Issued Oct. 11, 2011 in PCT/JP11/003833 Filed Jul. 5, 2011.
International Search Report Issued Oct. 11, 2011 in PCT/JP11/003833 Filed Jul. 5, 2011.
Combined Chinese Office Action and Search Report issued Jul. 2, 2014 in Patent Application No. 201180033851.0 (with English language translation and English translation of categories of cited documents).
Combined Chinese Office Action and Search Report issued Oct. 18, 2013 Patent Application No. 201180033851.0 (with English language translation).

\* cited by examiner

*Primary Examiner* — Jyothsna Venkat

(74) *Attorney, Agent, or Firm* — Oblon, McClelland, Maier & Neustadt, L.L.P.

(57) ABSTRACT

A hair cosmetic that contains, at a specific ratio, (A) a tertiary amine compound or a salt thereof, (B) an aliphatic alcohol having 12 to 26 carbon atoms, (C) a cationic group-containing copolymer obtainable by radical polymerization of a specific nonionic group-containing vinyl monomer, a specific cationic group-containing vinyl monomer, and a specific crosslinkable vinyl monomer as essential, and water.

6 Claims, No Drawings

HAIR COSMETIC

CROSS REFERENCE TO RELATED APPLICATION

This application is a 371 of PCT/JP2011/003833, filed on Jul. 5, 2011, and claims priority to Japanese Patent Application No. 2010-156198, filed on Jul. 8, 2010.

TECHNICAL FIELD

The present invention relates to a hair cosmetic.

BACKGROUND ART

It is known that massaging the scalp improves blood flow, enhances metabolism and provides an effect such as softening of the scalp. A relaxing effect is also obtainable by massaging. However, when massaging the scalp, a hair is sometimes damaged due to the hair being tangled or knotted.

On the other hand, in order to suppress tangling of the hair and facilitate smooth running through of fingers, hair cosmetics such as a hair shampoo, a hair rinse, a hair conditioner, a hair treatment, a hair cream, and a hair pack are widely used (for example, Patent Document 1).

RELATED DOCUMENTS

Patent Documents

Patent Document 1: Japanese Patent Publication No. 2003-327513
Patent Document 2: Japanese Patent Publication No. 6-48916

SUMMARY OF THE INVENTION

The present invention, therefore, provides a hair cosmetic that contains components (A) to (C) below:
(A) a tertiary amine compound or a salt thereof at 0.3 to 5 mass %
(B) an aliphatic alcohol having 12 to 26 carbon atoms at 1 to 15 mass %
(C) a cationic group-containing copolymer obtainable by radical polymerization of at least one type of nonionic group-containing vinyl monomer represented by general formula (I) or (II), at least one type of cationic group-containing vinyl monomer represented by general formula (III) or (IV), and at least one type of crosslinkable vinyl monomer having at least two groups selected from a vinyl group, an acryloyl group, a methacryloyl group, and an allyl group in the molecule as essential constituent monomers at 0.05 to 2 mass %, and water,
the mass ratio of the component (A) and the component (C) being (A)/(C)=3 to 46.

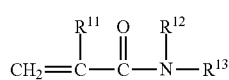

Wherein, in the general formula (I), $R^{11}$ represents a hydrogen atom or a methyl group, and $R^{12}$ and $R^{13}$ are identical or different and represent a hydrogen atom, or a straight chain or branched alkyl group or alkenyl group having 1 to 4 carbon atoms.

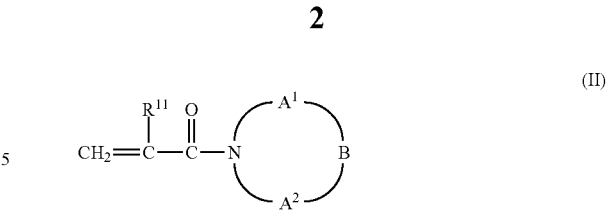

Wherein, in the general formula (II), $R^{11}$ represents a hydrogen atom or a methyl group, $A^1$ and $A^2$ are identical or different and represent a group represented by the formula —$(CH_2)_m$— (m represents an integer of 2 to 6), and B represents an —O— or —$CH_2$— group.

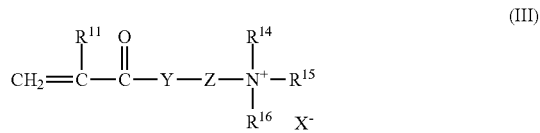

Wherein, in the general formula (III), $R^{11}$ represents a hydrogen atom or a methyl group, $R^{14}$ and $R^{15}$ are identical or different and represent an alkyl group or alkenyl group having 1 to 4 carbon atoms, $R^{16}$ represents a hydrogen atom or an alkyl group having 1 to 4 carbon atoms, Y represents an —O—, —NH—, —$CH_2$—, or —O—$CH_2CH(OH)$— group, Z represents a straight chain or branched chain alkylene group having 1 to 4 carbon atoms (0 to 3 carbon atoms when Y is —$CH_2$—), and X represents a conjugate base of an acid, a halogen atom, or an alkyl sulfate group having 1 to 4 carbon atoms.

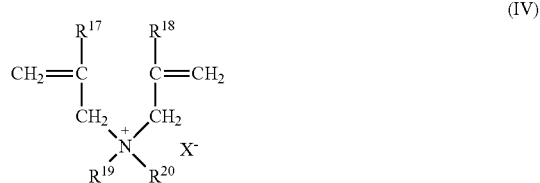

Wherein, in the general formula (IV), $R^{17}$ and $R^{18}$ are identical or different and represent a hydrogen atom or a methyl group, $R^{19}$ and $R^{20}$ are identical or different and represent a hydrogen atom or an alkyl group having 1 to 4 carbon atoms, and X represents a conjugate base of an acid, a halogen atom, or an alkyl sulfate group having 1 to 4 carbon atoms.

DESCRIPTION OF EMBODIMENTS

However, when massaging of the scalp using a conventional hair cosmetic, during the course of massaging the spreadability of the hair cosmetic is degraded, slipperiness of the hair reduces as time elapses, and a problem of hair becoming tangled around the fingers, a brush, and the like sometimes occurs. Because of this, massaging cannot be continued, and a sufficient massaging effect cannot be obtained in some cases.

The present inventors have found that by the use in combination, within a specific range, of a tertiary amine compound or a salt thereof, an aliphatic alcohol having 12 to 22 carbon atoms, and a specific cationic polymer, the slipperiness of the hair is sustained, tangling of the hair is therefore suppressed, and massaging can be continued.

Furthermore, in accordance with the present invention, there is provided a method for using a hair cosmetic, the method including applying the above hair cosmetic according to the present invention to the scalp and carrying out massaging.

Moreover, in accordance with the present invention, there is provided a method for using a hair cosmetic, the method including applying the hair cosmetic according to the present invention to the scalp by coating and then rinsing off.

In accordance with the present invention, there can be provided a hair cosmetic that, when massaging the scalp, enables tangling or knotting of the hair to be suppressed, massaging of the scalp to be continued, and obtains sufficient massaging effect.

An embodiment of the present invention is explained below.

(Hair Cosmetic)

Examples of components of the hair cosmetic used in the present invention include those below.

Component (A) is a tertiary amine compound or a salt thereof. This enables the hair to become smooth during application to the scalp or the hair or during subsequent rinsing.

As the tertiary amine compound, one represented by general formula (2) can be cited.

Wherein, in the general formula (2), $R^1$ represents a straight chain or branched chain alkyl group, alkenyl group, or aliphatic acyloxy(polyethoxy)ethyl group having 8 to 35 carbon atoms in total, which may be divided via a functional group represented by —OCO—, —COO—, —O— or —CONH—, or substituted with —OH, $R^2$ represents an alkyl group or hydroxyalkyl group having 1 to 22 carbon atoms, or a polyoxyethylene group having a total number of moles added of not greater than 10, and the 2 $R^2$s may be identical or different.

As the tertiary amine compound represented by the general formula (2), a salt of a tertiary amine formed by means of an organic acid and/or an inorganic acid may be used, or an acid may be formulated in the hair cosmetic of the present invention so that a salt is famed in the composition at the same time as adjustment of the pH. Examples of such an acid include an acid having a short chain alkyl group such as an alkylphosphoric acid, an alkylsulfonic acid, or an alkylsulfuric acid; an acidic amino acid such as L-glutamic acid or L-aspartic acid; pyroglutamic acid; an aromatic acid such as benzoic acid or p-toluenesulfonic acid; a hydroxy acid such as glycolic acid, lactic acid, glyceric acid, gluconic acid, pantothenic acid, malic acid, tartaric acid, or citric acid; and, in addition, phosphoric acid, hydrochloric acid, acetic acid, and succinic acid. Among them, an organic acid is preferable, an acidic amino acid, pyroglutamic acid, and a hydroxy acid are more preferable, and a hydroxy acid is even more preferable, in terms of exhibiting an effect of moisturizing and softening the hair.

Specific examples of the tertiary amine compound as the component (A) include at least any one of the tertiary amine compounds (i) to (iii) below (or a salt thereof).

(i) Hydroxy Ether Alkylamine (or a Salt Thereof)

Examples include a compound represented by general formula (3) below and a salt thereof.

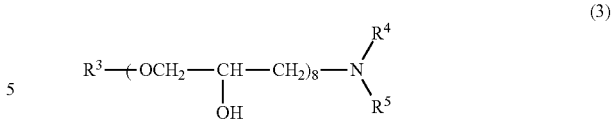

Wherein, in the general formula (3), $R^3$ represents a straight chain or branched chain alkyl group or alkenyl group having 6 to 24 carbon atoms, and $R^4$ and $R^5$ are identical or different and represent an alkyl group having 1 to 6 carbon atoms or -$(AO)_f$H (A represents an alkylene group having 2 to 4 carbon atoms, f represents a number from 1 to 6, the f As may be identical or different, and they may be in any order). e represents a number from 1 to 5.

Specific examples include hexadecyloxy(2-hydroxypropyl)dimethylamine and a salt thereof, and octadecyloxy(2-hydroxypropyl)dimethylamine and a salt thereof.

(ii) Ether Amine (or a Salt Thereof)

Examples include a compound represented by general formula (4) below and a salt thereof.

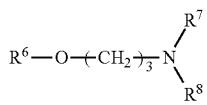

Wherein, in the general formula (4), $R^6$ represents a straight chain or branched chain alkyl group or alkenyl group having 6 to 24 carbon atoms, and $R^7$ and $R^8$ are identical or different and represent an alkyl group having 1 to 6 carbon atoms or -$(AO)_g$H (A represents an alkylene group having 2 to 4 carbon atoms, g represents a number from 1 to 6, the g As may be identical or different, and they may be in any order).

Specific examples include N,N-dimethyl-3-hexadecyloxypropylamine and a salt thereof, and N,N-dimethyl-3-octadecyloxypropylamine and a salt thereof.

(iii) Alkylamidoamine (or a Salt Thereof)

Examples include a compound represented by general formula (5) below and a salt thereof.

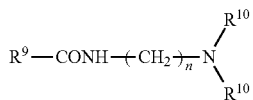

Wherein, in the general formula (5), $R^9$ represents an aliphatic hydrocarbon group having 11 to 23 carbon atoms, the $R^{10}$s are identical or different and represent a hydrogen atom or an alkyl group having 1 to 4 carbon atoms, and n represents a number from 2 to 4.

Specific examples include N-(3-(dimethylamino)propyl) docosanamide and a salt thereof and N-(3-(dimethylamino) propyl)stearamide and a salt thereof.

Among the tertiary amine compounds cited in (i) to (iii) above, (ii) the ether amine (or a salt thereof) and (iii) the alkylamidoamine (or a salt thereof) are preferable from the viewpoint of smoothness during application and during rinsing. Among them, (ii) the ether amine (or a salt thereof) is more preferable. This makes the hair more resistant to tangling when massaging the scalp. Furthermore, N,N-dimethyl-3-hexadecyloxypropylamine or a salt thereof and N,N-dimethyl-3-octadecyloxypropylamine or a salt thereof are preferable.

With regard to the component (A), one or more types of tertiary amine compound may be used in combination.

The content of the component (A) is preferably at least 0.3 mass % of the entire hair cosmetic, more preferably at least 0.5 mass %, and even more preferably at least 1 mass %, from the viewpoint of imparting smoothness. On the other hand, the hair cosmetic preferably contains component (A) at not greater than 5 mass % from the viewpoint of obtaining a good feel during use, and more preferably not greater than 3 mass % from the viewpoint of slipperiness of the hair at the initial stage and the balance of ease of spreading and ease of diffusion of the hair cosmetic.

The component (B) is now explained.

The component (B) is an aliphatic alcohol having 12 to 26 carbon atoms. This enables the hair to be made smooth during application to the scalp or the hair and during subsequent rinsing.

Furthermore, an aliphatic alcohol having a straight chain or branched chain alkyl group or alkenyl group is preferable, and an aliphatic alcohol having a straight chain or branched chain alkyl group or alkenyl group having 16 to 22 carbon atoms is more preferable, from the viewpoint of imparting smoothness to the hair during application to the scalp or the hair, during subsequent rinsing, and after drying. An aliphatic alcohol having a straight chain or branched chain alkyl group or alkenyl group having 16 to 18 carbon atoms is even more preferable. Specifically, cetyl alcohol and stearyl alcohol are preferable. Cetyl alcohol is more preferable.

The aliphatic alcohol contains one hydroxy group and does not contain two or more hydroxy groups.

The content of the component (B) is preferably at least 1 mass % of the entire hair cosmetic, and more preferably at least 3 mass %, from the viewpoint of imparting smoothness. Furthermore, the hair cosmetic contains the component (B) at not greater than 15 mass % from the viewpoint of obtaining a good feel during use, and more preferably not greater than 10 mass % from the viewpoint of slipperiness of the hair at the initial stage and the balance of ease of spreading and ease of diffusion of the hair cosmetic.

The component (C) is now explained.

The component (C) is a cationic group-containing copolymer obtainable by radical polymerization of at least one type of nonionic group-containing vinyl monomer represented by general formula (I) or (II), at least one type of cationic group-containing vinyl monomer represented by general formula (III) or (IV), and at least one type of crosslinkable vinyl monomer having at least two groups selected from a vinyl group, an acryloyl group, a methacryloyl group, and an allyl group in the molecule as essential constituent monomers. Due to the component (C) being contained in the hair cosmetic, spreading of the hair cosmetic is sustained, slipperiness of the hair is also sustained, the hair cosmetic penetrates well into the hair root, and tangling and knotting of the hair by massaging can be suppressed. Furthermore, dripping of the hair cosmetic from the scalp can be suppressed. Because of this, massaging can be continued, and a sufficient massaging effect is obtainable. Moreover, a frictional feel of the hair is suppressed during or after rinsing off the hair cosmetic.

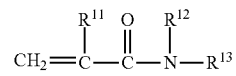

(I)

Wherein, in the formula (I), $R^{11}$ represents a hydrogen atom or a methyl group, and $R^{12}$ and $R^{13}$ are identical or different and represent a hydrogen atom or a straight chain or branched alkyl group or alkenyl group having 1 to 4 carbon atoms.

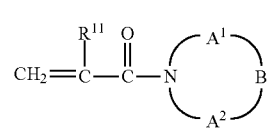

(II)

Wherein, in the general formula (II), $R^{11}$ represents a hydrogen atom or a methyl group, $A^1$ and $A^2$ are identical or different and represent a group represented by the formula $-(CH_2)_m-$ (m represents an integer of 2 to 6), and B represents an $-O-$ or $-CH_2-$ group.

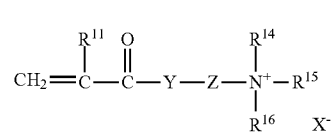

(III)

Wherein, in the general formula (III), $R^{11}$ represents a hydrogen atom or a methyl group, $R^{14}$ and $R^{15}$ are identical or different and represent an alkyl group or alkenyl group having 1 to 4 carbon atoms, $R^{16}$ represents a hydrogen atom or an alkyl group having 1 to 4 carbon atoms, Y represents an $-O-$, $-NH-$, $-CH_2-$, or $-O-CH_2CH(OH)-$ group, Z represents a straight chain or branched chain alkylene group having 1 to 4 carbon atoms (0 to 3 carbon atoms when Y is $-CH_2-$), and X represents a conjugate base of an acid, a halogen atom, or an alkyl sulfate group having 1 to 4 carbon atoms.

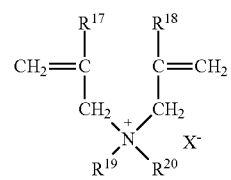

(IV)

Wherein in the general formula (IV), $R^{17}$ and $R^{18}$ are identical or different and represent a hydrogen atom or a methyl group, $R^{19}$ and $R^{20}$ are identical or different and represent a hydrogen atom or an alkyl group having 1 to 4 carbon atoms, and X represents a conjugate base of an acid, a halogen atom, or an alkyl sulfate group having 1 to 4 carbon atoms.

Furthermore, preferred examples of one embodiment of the cationic group-containing copolymer include an N,N-dimethylaminoethyl methacrylate diethyl sulfate salt/N,N-dimethylacrylamide/polyethylene glycol dimethacrylate copolymer represented by formula (V) below from the viewpoint of smoothness of the hair being sustained and tangling and knotting of the hair by massaging being suppressed.

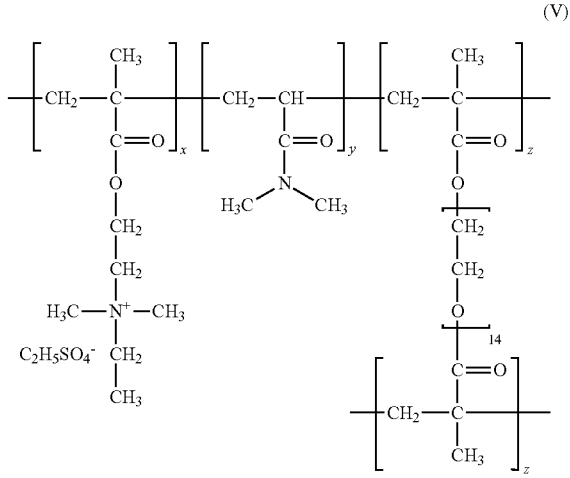

(V)

Wherein, in the formula (V), x, y, and z are identical or different and are positive numbers, the molar ratio being x/y=1/9 to 5/5 and (x+y+z)/z=1/0.1 to 1/0.002.

Examples of commercial products include Sofcare KG-301W (Kao Corporation) and Sofcare KG-101W-E (Kao Corporation).

The content of the component (C) is at least 0.05 mass % of the entire hair cosmetic from the viewpoint of spreading of the hair cosmetic being sustained, slipperiness of the hair being sustained, good penetration of the hair cosmetic to the hair root, and suppression of tangling or knotting of the hair by massaging, and is preferably at least 0.1 mass % from the viewpoint of foam retention. On the other hand, the hair cosmetic contains the component (C) at not greater than 2 mass %, preferably not greater than 0.75 mass %, and more preferably not greater than 0.5 mass %, from the viewpoint of preventing a frictional feel of the hair during and after rinsing off the hair cosmetic and obtaining a good feel during use.

Furthermore, the mass ratio of the component (A) and the component (C) is preferably (A)/(C)=3 to 46 from the viewpoint of spreading of the hair cosmetic being sustained, slipperiness of the hair also being sustained, the hair cosmetic penetrating well into the hair root, and tangling and knotting of the hair by massaging being suppressed, and is more preferably 4 to 18 from the viewpoint of prevention of dripping from the scalp and the balance with frictional feel when finished.

Furthermore, the water content is preferably 50 to 98 mass % in the hair cosmetic of the present invention, and more preferably 60 to 95 mass %.

Moreover, the hair cosmetic of the present invention may contain the components below in addition to the components (A) to (C) and water.

For example, the hair cosmetic of the present invention may contain component (D), which is a betaine-based amphoteric surfactant. This enables the foam retention of the hair cosmetic to be improved and massaging to be continued for longer. Furthermore, foaming improves the slipperiness of the hair.

As the betaine-based amphoteric surfactant, a betaine-based surfactant such as an imidazoline-based betaine, an alkyldimethylaminoacetic acid betaine, a fatty acid amidopropyl betaine, or an alkylhydroxysulfobetaine is preferable. An alkylhydroxysulfobetaine is more preferable from the viewpoint of improving foam retention, and preferably has an alkyl group having 10 to 16 carbon atoms. Laurylhydroxysulfobetaine is even more preferable.

The content of the component (D) is preferably at least 0.05 mass % of the entire hair cosmetic, more preferably at least 0.15 mass %, and even more preferably at least 0.3 mass %, from the viewpoint of making foam retention sustained. Furthermore, the content of the component (D) is preferably not greater than 2 mass % of the entire hair cosmetic, and more preferably not greater than 1.5 mass %, from the viewpoint of obtaining a good feel during use.

Furthermore, the hair cosmetic of the present invention may further contain component (E), which is an organic carboxylic acid. This enables the hair to be smooth during application to the scalp or the hair and during subsequent rinsing. As the organic carboxylic acid, one having 2 to 8 carbon atoms is preferable. Examples thereof include an α-hydroxy acid, glycolic acid, lactic acid, tartaric acid, malic acid, levulinic acid, acetic acid, maleic acid, and fumaric acid. Among them, an α-hydroxy acid, glycolic acid, malic acid, and lactic acid are preferable, and malic acid and lactic acid are even more preferable. The organic carboxylic acid may be in the form of a salt. Examples of such a salt include salts with an alkali metal, an alkaline earth metal, ammonia, an organic amine compound, and the like. With regard to the organic acid or a salt thereof, two or more types may be used in combination.

The content of the component (E) is preferably at least 0.1 mass % of the entire hair cosmetic, and more preferably at least 0.5 mass %, from the viewpoint of making the hair smooth during application to the scalp or the hair and during subsequent rinsing. Furthermore, the content of the component (E) is not greater than 5 mass % of the entire hair cosmetic, and preferably not greater than 3 mass %, from the viewpoint of obtaining a good feel during use.

The pH of the hair cosmetic of the present invention when diluted 20 times by mass is preferably 1 to 5. This enables the hair to become smooth during application to the scalp or the hair or during subsequent rinsing. The pH is even more preferably 3 to 4.

With regard to a conventional hair cosmetic, since its spreadability decreases as time elapses while being spread over the hair or the scalp, tangling or knotting of the hair easily occurs, and the hair or the scalp might be damaged in some cases. Because of this, massaging cannot be continued.

In contrast therewith, the hair cosmetic of the present invention can improve spreading of the hair cosmetic and sustain slipperiness of the hair since it employs in combination, in a specific range, a tertiary amine compound or a salt thereof, an aliphatic alcohol having 12 to 22 carbon atoms, and a specific cationic polymer. This enables tangling or knotting of the hair even when massaging is continued to be suppressed, massaging can be continued, and a sufficient massaging effect is obtainable. Furthermore, since the hair cosmetic of the present invention tends to remain on the scalp, with the synergic effect of massaging, an effect of the scalp becoming smooth and soft is also obtainable.

(Others)

With regard to the hair cosmetic of the present invention, other than the above-mentioned components, a surfactant, an oil-based component, a cationic polymer and, furthermore, a higher fatty acid ester, a higher fatty acid, glycerol, a moisturizing agent, a polysaccharide, a polypeptide, a pearlescent agent, a solvent, a liquid crystal-forming base, an aromatic sulfonic acid, a coloring agent, a fragrance, a propellant, a chelating agent, a pH adjusting agent, a preservative, an antidandruff agent, and the like may be formulated as appropriate. Examples of the antidandruff agent include zinc pyrithione and piroctone olamine.

As the surfactant other than the above-mentioned components, an anionic surfactant, a nonionic surfactant, an amphoteric surfactant, and a cationic surfactant may be contained, and two or more types of these surfactants may be used in combination.

The anionic surfactant is preferably a sulfuric acid-based, sulfonic acid-based, carboxylic acid-based, phosphoric acid-based, or amino acid-based surfactant. Examples include an alkyl sulfate, a polyoxyalkylene alkyl ether sulfate, a polyoxyalkylene alkenyl ether sulfate, an alkyl sulfosuccinate ester, an alkyl polyoxyalkylene sulfosuccinate ester, a polyoxyalkylene alkyl phenyl ether sulfate, an alkanesulfonate, an acyl isethionate, an acylmethyltaurate, a higher fatty acid salt, a polyoxyalkylene alkyl ether acetate, an alkylphosphate, a polyoxyalkylene alkyl ether phosphate, an acylglutamate, an alanine derivative, a glycine derivative, and an arginine derivative. Among them, a polyoxyethylene alkyl ether sulfate, a polyoxyethylene alkenyl ether sulfate, an alkyl sulfate, an acyl isethionate, an acylmethyltaurate, a higher fatty acid salt, a polyoxyalkylene alkyl ether acetate, an alkylphosphate, a polyoxyalkylene alkyl ether phosphate, an acylglutamate, and an alkylalanine derivative are preferable, and those represented by general formula (6) or (7) are even more preferable.

$$R^{21}O(CH_2CH_2O)_pSO_3M \qquad (6)$$

$$R^{22}OSO_3M \qquad (7)$$

Wherein, in the general formula (6) and (7), $R^{21}$ represents for example an alkyl group or alkenyl group having 10 to 18 carbon atoms, $R^{22}$ represents an alkyl group having 10 to 18 carbon atoms, M represents an alkali metal, an alkaline earth metal, ammonium, an alkanolamine, or a basic amino acid, and p is the average number of moles of addition of the ethylene oxide and represents a number from 1 to 5.

Examples of the nonionic surfactant include a polyoxyalkylene sorbitan fatty acid ester, a polyoxyalkylene sorbitol fatty acid ester, a polyoxyalkylene glycerol fatty acid ester, a polyoxyalkylene fatty acid ester, a polyoxyalkylene alkyl ether, a polyoxyalkylene alkyl phenyl ether, a polyoxyalkylene (hardened) castor oil, a sucrose fatty acid ester, a polyglycerol alkyl ether, a polyglycerol fatty acid ester, a fatty acid alkanolamide, and an alkyl glucoside. Among them, an alkyl glucoside, a polyoxyalkylene C8-C20 fatty acid ester, a polyoxyethylene sorbitan fatty acid ester, a polyoxyethylene hardened castor oil, and a fatty acid alkanolamide are preferable. As the alkyl glucoside, one having an alkyl group having 8 to 14 carbon atoms and a degree of condensation of sugar (glucose) of 1 to 2 is preferable. As the fatty acid alkanolamide, one having an acyl group having 8 to 18 carbon atoms is preferable, and one having 10 to 16 carbon atoms is more preferable; either a monoalkanolamide or a dialkanolamide may be used, and one having a hydroxyalkyl group having 2 to 3 carbon atoms is preferable. Specific examples of the fatty acid alkanolamide include oleic acid diethanolamide, palm kernel oil fatty acid diethanolamide, coconut oil fatty acid diethanolamide, lauric acid diethanolamide, polyoxyethylene coconut oil fatty acid monoethanolamide, coconut oil fatty acid monoethanolamide, lauric acid monoisopropanolamide, lauric acid monoethanolamide, palm kernel oil fatty acid methyl ethanolamide, and coconut oil fatty acid methyl ethanolamide.

Examples of the oil-based component other than the above-mentioned components include a silicone, an ester oil, a hydrocarbon, a glyceride, a vegetable oil, an animal fat, a lanolin derivative, and a higher fatty acid ester.

Examples of the ester oil include an ester oil having 8 to 40 carbon atoms in total, preferably an ester of a fatty acid having 8 to 20 carbon atoms in total and an alcohol having 1 to 20 carbon atoms, and even more preferably isopropyl palmitate and isopropyl myristate.

Examples of the silicone include (a) a polydimethylsiloxane described in Japanese Patent Publication No. 6-48916, (b) a polymethylphenylsiloxane, (c) an amino-modified silicone (examples of aqueous emulsions including SM8704C (Dow Corning Toray Silicone Co., Ltd.) and DC939 (Dow Corning Toray Silicone Co., Ltd.)), (d) a fatty acid-modified polysiloxane, (e) an alcohol-modified silicone, (f) an aliphatic alcohol-modified polysiloxane, (g) a polyether-modified silicone, (h) an epoxy-modified silicone, (i) a fluorine-modified silicone, (j) a cyclic silicone, (k) an alkyl-modified silicone, and (l) an oxazoline-modified silicone.

Among them, (l) an oxazoline-modified silicone is preferable, an oxazoline-modified silicone formed by bonding a poly N-acylalkyleneimine formed from a repeating unit represented by general formula (8) below to at least one silicon atom at the terminal or in the side chain of an organopolysiloxane segment via a heteroatom-containing alkylene group is more preferable, and an N-propionyl polyethyleneimine/polymethylsiloxane copolymer is even more preferable, from the viewpoint of providing slipperiness of the hair. Furthermore, one having a ratio of N-propionyl polyethyleneimine and polymethylsiloxane of 50:50 to 2:98 is preferable.

(8)

Wherein, in the general formula (8), $R^{23}$ represents a hydrogen atom or an alkyl group, cycloalkyl group, aralkyl group, or aryl group having 1 to 22 carbon atoms, and q represents 2 or 3.

Examples of the cationic polymer other than the above-mentioned components include a cationized cellulose derivative, a cationic starch, and a cationized guar gum derivative, from the viewpoint of providing slipperiness of the hair. With regard to these cationic polymers, two or more types may be used in combination.

In one example of a preferred embodiment of the hair cosmetic of the present invention, the component (A) is an ether amine (or a salt thereof), the component (B) is cetyl alcohol or stearyl alcohol, the component (C) is an N,N-dimethylaminoethyl methacrylate diethyl sulfate salt/N,N-dimethylacrylamide/polyethylene glycol dimethacrylate copolymer represented by the formula (V), and the component (D) is laurylhydroxysulfobetaine, from the viewpoint of massaging of the scalp being continued and a sufficient massaging effect being given.

The hair cosmetic of the present invention may be produced by a standard method and made into a desired form such as an aqueous solution, an ethanol solution, an emulsion, a suspension, a gel, a liquid crystal, a solid, an aerosol foam, or a spray. Furthermore, as a hair cleansing agent composition, a product such as a hair shampoo may be produced, and as a hair cosmetic other than the hair cleansing agent composition, a product such as a hair rinse, a hair conditioner, a hair treatment, a hair pack, a hair cream, a hair color, a conditioning mousse, a hair mousse, a hair spray, a leave-on treatment, a wax, a tonic, or a hair dye may be produced.

A method for using the hair cosmetic is not particularly limited, and the hair cosmetic may be applied to the scalp and subsequently made to contact the hair while pressing and spreading on the scalp in a zigzag manner using the fingers, a brush, and the like, thus spreading the hair cosmetic on the hair.

Furthermore, the method for using the hair cosmetic of the present invention may include for example applying the hair cosmetic to the scalp and carrying out massaging.

Moreover, the method for using the hair cosmetic of the present invention may include for example rinsing off the hair cosmetic after it has been applied to the scalp by coating.

In addition, the present invention is not limited to the above-mentioned embodiments, and modification, improvement, and the like that can achieve the object of the present invention are included in the present invention.

For example, the present invention includes the following embodiments:
(1) Use of the hair cosmetic of the present invention for massaging the scalp.
(2) Use of the hair cosmetic of the present invention for production of a massaging agent for the scalp.
(3) Use of the hair cosmetic of the present invention for rinsing off after being applied to the scalp.
(4) Use of the hair cosmetic of the present invention for production of a hair cosmetic that is rinsed off after being applied to the scalp.

EXAMPLES

The present invention is more specifically explained below by reference to Examples, but the present invention is not limited to these Examples. '%' in the Examples and Comparative Examples means 'mass %' unless otherwise specified. Furthermore, each formulation has a total amount of 100 mass %.

Examples 1 to 8 and Comparative Examples 1 to 5

Hair cosmetics having the compositions shown in Table 1 and Table 2 were prepared by a standard method and evaluated by the evaluation methods below. The results are shown in Table 1 and Table 2. The pH is the value at 25° C. when diluted 20 times by mass with water.
(Evaluation Methods)
(1) Ease of Spreading of Hair Cosmetic at Initial Stage A bundle of human hair having a length of 25 cm, a width of 5.5 cm, and a weight of 10 g was lightly rinsed with hot water at 40° C., excess moisture was then removed, and 0.5 g of the hair cosmetic was applied to and spread on the bundle of human hair. Immediately after that, ease of spreading of the hair cosmetic was subjected to sensory evaluation using the five criteria below. Evaluation was carried out by five people, and the average value was obtained. An average of at least 4.0 was 'oo', at least 3.2 but less than 4.0 was 'o', at least 2.5 but less than 3.2 was 'Δ', and less than 2.5 was 'x'.
5: spread well
4: spread fairly well
3: spread normally
2: did not spread very much
1: difficult to spread
(2) Sustained Spreading of Hair Cosmetic A bundle of human hair having a length of 25 cm, a width of 5.5 cm, and a weight of 10 g was lightly rinsed with hot water at 40° C., excess moisture was then removed, and 0.5 g of the hair cosmetic was applied to and spread on the bundle of human hair. 2 minutes after that, ease of spreading (sustained) of the hair cosmetic was subjected to sensory evaluation using the five criteria below. Evaluation was carried out by five people, and the average value was obtained. An average of at least 4.0 was 'oo', at least 3.2 but less than 4.0 was 'o', at least 2.5 but less than 3.2 was 'Δ', and less than 2.5 was 'x'.
5: spread well
4: spread fairly well
3: spread normally
2: did not spread very much
1: difficult to spread
(3) Penetration of Hair Cosmetic to Hair Root Human hair was lightly rinsed with hot water at 40° C., excess moisture was then removed, and 1 g of the hair cosmetic was applied to the hair by coating and made to spread. Penetration of the hair cosmetic to the root of the hair at that time was subjected to sensory evaluation using the five criteria below. Evaluation was carried out by five people, and the average value was obtained. An average of at least 4.0 was 'oo', at least 3.2 but less than 4.0 was 'o', at least 2.5 but less than 3.2 was 'Δ', and less than 2.5 was 'x'.
5: penetrated well
4: penetrated fairly well
3: penetrated normally
2: did not penetrate very much
1: did not penetrate
(4) Slipperiness of Hair at Initial Stage A bundle of human hair having a length of 25 cm, a width of 5.5 cm, and a weight of 10 g was lightly rinsed with hot water at 40° C., excess moisture was then removed, and 0.5 g of the hair cosmetic was applied to and spread on the bundle of human hair. Immediately after that, the slipperiness of the bundle of human hair was subjected to sensory evaluation using the five criteria below. Evaluation was carried out by five people, and the average value was obtained. An average of at least 4.0 was 'oo', at least 3.2 but less than 4.0 was 'o', at least 2.5 but less than 3.2 was 'Δ', and less than 2.5 was 'x'.
5: very slippery
4: fairly slippery
3: normally slippery
2: not very slippery
1: not slippery
(5) Sustained Slipperiness of Hair A bundle of human hair having a length of 25 cm, a width of 5.5 cm, and a weight of 10 g was lightly rinsed with hot water at 40° C., excess moisture was then removed, and 0.5 g of the hair cosmetic was applied to and spread on the bundle of human hair. 2 minutes after that, the slipperiness (sustained) of the bundle of human hair was subjected to sensory evaluation using the five criteria below. Evaluation was carried out by five people, and the average value was obtained. An average of at least 4.0 was 'oo', at least 3.2 but less than 4.0 was 'o', at least 2.5 but less than 3.2 was 'Δ', and less than 2.5 was 'x'.
5: very slippery
4: fairly slippery
3: normally slippery
2: not very slippery
1: not slippery
(6) Frictional Feel in Finished State After Rinsing A bundle of human hair having a length of 25 cm, a width of 5.5 cm, and a weight of 10 g was lightly rinsed with hot water at 40° C., excess moisture was then removed, and 0.5 g of the hair cosmetic was applied to and spread on the bundle of human hair. After that, the bundle of human hair having the hair cosmetic attached thereto was rinsed with hot water at 40° C. at a flow rate of 2 L/min, and the absence of a frictional feel of the rinsed bundle of human hair in a finished state was subjected to sensory evaluation using the five criteria below. Evaluation was carried out by five people, and the average value was obtained. An average of at least 4.0 was 'oo', at least 3.2 but less than 4.0 was 'o', at least 2.5 but less than 3.2 was 'Δ', and less than 2.5 was 'x'.

5: no frictional feel
4: little frictional feel
3: normal frictional feel
2: some frictional feel
1: frictional feel (7) Foam Retention A bundle of human hair having a length of 25 cm, a width of 5.5 cm, and a weight of 10 g was lightly rinsed with hot water at 40° C., excess moisture was then removed, and 0.5 g of the hair cosmetic was foamed and applied to and spread on the bundle of human hair. After that, foam retention for 2 minutes was subjected to sensory evaluation using the five criteria below. Evaluation was carried out by five people, and the average value was obtained. An average of at least 4.0 was 'oo', at least 3.2 but less than 4.0 was 'o', at least 2.5 but less than 3.2 was 'Δ', and less than 2.5 was 'x'.

5: good foam retention
4: fairly good foam retention
3: normal foam retention
2: not very good foam retention
1: poor foam retention

TABLE 1

|  |  |  | Example |  |  |  |  |  |  |  |
|---|---|---|---|---|---|---|---|---|---|---|
|  |  |  | 1 | 2 | 3 | 4 | 5 | 6 | 7 | 8 |
| Content (mass %) | Component (A) | N,N-Dimethyl-3-octadecyloxypropylamine (Farmin DM E-80 (Kao Corporation, 90%)) | 1.4 | — | 1.4 | 1.4 | 1.4 | 3.7 | 1.2 | 1.4 |
|  |  | N-(3-Dimethylamino)propyl)stearamide (Palner SDPA (Miyoshi Oil & Fat Co., Ltd., 100%)) | — | 1.4 | — | — | — | — | — | — |
|  | Component (B) | Cetyl alcohol (Kalcol 6870 (Kao Corporation, 100%)) | 5 | 5 | — | 5 | 5 | 11 | 4 | 5 |
|  |  | Stearyl alcohol (Kalcol 8098 (Kao Corporation, 100%)) | — | — | 5 | — | — | — | — | — |
|  | Component (C) | N,N-Dimethylaminoethyl methacrylate diethyl sulfate salt/N,N-dimethyl acrylamide/polyethylene glycol dimethacrylate copolymer (Sofcare KG-101W-E (Kao Corporation, 2.4%)) | 0.26 | 0.26 | 0.26 | 0.081 | 0.36 | 0.081 | 0.36 | 0.47 |
|  | Other components | O-[2-Hydroxy-3-(trimethylammonio) propyl]hydroxyethylcellulose chloride (Poiz C-60H (Kao Corporation, 90%)) | — | — | — | — | — | — | — | — |
|  |  | Laurylhydroxysulfobetaine (Amphitol 20HD (Kao Corporation, 30%)) | 0.74 | 0.74 | 0.74 | 0.74 | 0.74 | 0.74 | 0.74 | 0.74 |
|  |  | Polyoxypropylene (3) octyl ether (Sofcare GP-1 (Kao Corporation, 100%)) | 0.1 | 0.1 | 0.1 | 0.1 | 0.1 | 0.1 | 0.1 | 0.1 |
|  |  | N-Propionylpolyethyleneimine/poly methylsiloxane copolymer (OS-88E-E (Kao Corporation, 30%)) | 0.23 | 0.23 | 0.23 | 0.23 | 0.23 | 0.23 | 0.23 | 0.23 |
|  |  | Isopropyl palmitate (Exceparl IPP (Kao Corporation, 100%)) | 0.2 | 0.2 | 0.2 | 0.2 | 0.2 | 0.2 | 0.2 | 0.2 |
|  |  | High Mwt. polyethylene glycol (Polyox WSR N-60K (The Dow Chemical Company, 97%)) | 0.14 | 0.14 | 0.14 | 0.14 | 0.14 | 0.14 | 0.14 | 0.14 |
|  |  | Hydroxyethylcellulose (HEC Daicel SE85OK (Daicel Chemical Industries, Ltd., 100%)) | 0.3 | 0.3 | 0.3 | 0.3 | 0.3 | 0.3 | 0.3 | 0.3 |
|  |  | Propylene glycol (cosmetic propylene glycol (ADEKA, 100%)) | 3 | 3 | 3 | 3 | 3 | 3 | 3 | 3 |
|  |  | Lactic acid (Musashino lactic acid 90 (Musashino Chemical Laboratory, Ltd., 90%)) | 1.3 | 1.3 | 1.3 | 1.3 | 1.3 | 1.8 | 1.3 | 1.3 |
|  |  | Fragrance | Appropriate amt. | Appropriate amt. | Appropriate amt. | Appropriate amt. | Appropriate amt. | Appropriate amt. | Appropriate amt. | Appropriate amt. |
|  |  | Water | Balance | Balance | Balance | Balance | Balance | Balance | Balance | Balance |
| mass ratio of (A)/(C) |  |  | 5.4 | 5.4 | 5.4 | 17.3 | 3.9 | 45.7 | 3.3 | 3.0 |
| pH* |  |  | 3.4 | 3.4 | 3.4 | 3.4 | 3.4 | 3.4 | 3.4 | 3.4 |
| Evaluation results | Ease of spreading of hair cosmetic at initial stage |  | oo | oo | oo | oo | oo | o | oo | oo |
|  | Sustained spreading of hair cosmetic |  | oo | oo | oo | o | oo | o | oo | oo |
|  | Penetration of hair cosmetic to hair root |  | oo | oo | oo | o | o | o | o | o |
|  | Slipperiness of hair at initial stage |  | oo | oo | oo | oo | oo | o | oo | o |
|  | Sustained slipperiness of hair |  | oo | oo | oo | o | oo | o | oo | oo |
|  | No frictional feel in finished state after rinsing |  | oo | oo | oo | o | o | oo | o | oo |
|  | Foam retention |  | oo | oo | oo | o | oo | o | oo | o |

*pH shown is the value at 25° C. when diluted 20 times by mass with water. Adjusted with potassium hydroxide The content of each component in the table is the value as 100% effective component.

TABLE 2

| | | | Comparative Example | | | | |
|---|---|---|---|---|---|---|---|
| | | | 1 | 2 | 3 | 4 | 5 |
| Content (mass %) | Component (A) | N,N-Dimethyl-3-octadecyloxypropylamine (Farmin DM E-80 (Kao Corporation, 90%)) | — | 1.4 | 1.4 | 1.4 | 1.4 |
| | | N-(3-Dimethylamino)propyl)stearamide (Palner SDPA (Miyoshi Oil & Fat Co., Ltd., 100%)) | — | — | — | — | — |
| | Component (B) | Cetyl alcohol (Kalcol 6870 (Kao Corporation, 100%)) | 5 | — | 5 | 5 | 5 |
| | | Stearyl alcohol (Kalcol 8098 (Kao Corporation, 100%)) | — | — | — | — | — |
| | Component (C) | N,N-Dimethylaminoethyl methacrylate diethyl sulfate salt/N,N-dimethylacrylamide/polyethylene glycol dimethacrylate copolymer (Sofcare KG-101W-E (Kao Corporation, 2.4%)) | 0.26 | 0.26 | — | 0.025 | — |
| | Other components | O-[2-Hydroxy-3-(trimethylammonio)propyl]hydroxyethylcellulose chloride (Poiz C-60H (Kao Corporation, 90%)) | — | — | — | — | 0.26 |
| | | Laurylhydroxysulfobetaine (Amphitol 20HD (Kao Corporation, 30%)) | 0.74 | 0.74 | 0.74 | 0.74 | 0.74 |
| | | Polyoxypropylene (3) octyl ether (Sofcare GP-1 (Kao Corporation, 100%)) | 0.1 | 0.1 | 0.1 | 0.1 | 0.1 |
| | | N-Propionylpolyethyleneimine/polymethyl siloxane copolymer (OS-88E-E (Kao Corporation, 30%)) | 0.23 | 0.23 | 0.23 | 0.23 | 0.23 |
| | | Isopropyl palmitate (Exceparl IPP (Kao Corporation, 100%)) | 0.2 | 0.2 | 0.2 | 0.2 | 0.2 |
| | | High Mwt. polyethylene glycol (Polyox WSR N-60K (The Dow Chemical Company, 97%)) | 0.14 | 0.14 | 0.14 | 0.14 | 0.14 |
| | | Hydroxyethylcellulose (HEC Daicel SE850K (Daicel Chemical Industries, Ltd., 100%)) | 0.3 | 0.3 | 0.3 | 0.3 | 0.3 |
| | | Propylene glycol (cosmetic propylene glycol (ADEKA, 100%)) | 3 | 3 | 3 | 3 | 3 |
| | | Lactic acid (Musashino lactic acid 90 (Musashino Chemical Laboratory, Ltd., 90%)) | 1.3 | 1.3 | 1.3 | 1.3 | 1.3 |
| | | Fragrance | Appropriate amount | Appropriate amount | Appropriate amount | Appropriate amount | Appropriate amount |
| | | Water | Balance | Balance | Balance | Balance | Balance |
| mass ratio of (A)/(C) | | | — | 5.4 | — | 56 | — |
| pH* | | | 3.4 | 3.4 | 3.4 | 3.4 | 3.4 |
| Evaluation Results | | Ease of spreading of hair cosmetic at initial stage | † | † | ○○ | ○○ | ○○ |
| | | Sustained spreading of hair cosmetic | † | † | x | Δ | x |
| | | Penetration of hair cosmetic to hair root | † | † | x | Δ | x |
| | | Slipperiness of hair at initial stage | † | † | ○○ | ○○ | ○○ |
| | | Sustained slipperiness of hair | † | † | x | Δ | x |
| | | No frictional feel in finished state after rinsing | † | † | ○○ | ○○ | ○○ |
| | | Foam retention | † | † | x | Δ | x |

*pH shown is the value at 25° C. when diluted 20 times by mass with water. Adjusted with potassium hydroxide
†: Formulated hair cosmetic separated, so evaluation of performance not possible
The content of each component in the table is the value as 100% effective component.

From Table 1, in the Examples, spreading of the hair cosmetic was good and sustained, the hair cosmetic was easy to spread, slipperiness of the hair could be sustained, and the foam retention was good. Furthermore, after the hair cosmetic was rinsed off, hardly any frictional feel of the hair occurred. It is clear from these results that in accordance with the hair cosmetic of the Examples, since massaging can be continued, a sufficient massaging effect can be obtained.

The invention claimed is:

1. A method for applying a hair cosmetic to the scalp of a subject, the method comprising applying a hair cosmetic to the scalp having hair thereon and carrying out massaging, wherein said hair cosmetic comprises:
    (A) from 1 to 5 mass % of an ether amine selected from the group consisting of N,N-dimethyl-3-hexadecyloxypropylamine or a salt thereof and N,N-dimethyl-3-octadecyloxypropylamine or a salt thereof;
    (B) from 3 to 15 mass % of an aliphatic alcohol having 16 to 18 carbon atoms;
    (C) from 0.05 to 0.5 mass % of a cationic group-containing copolymer which is an N,N-dimethylaminoethyl methacrylate diethyl sulfate salt/N,N-dimethylacrylamide/polyethylene glycol dimethacrylate copolymer of formula (V):

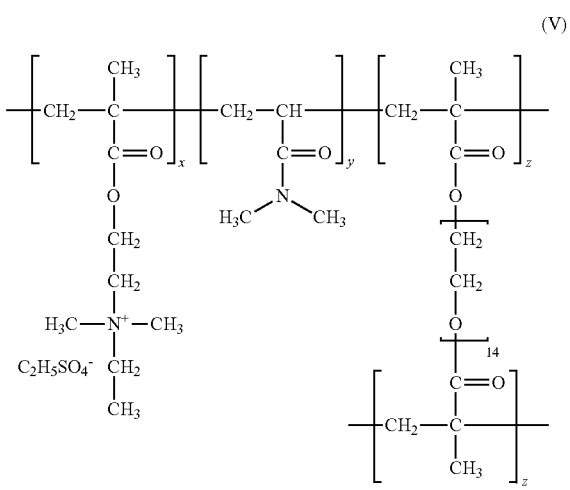

wherein, x, y, and z are identical or different and are positive numbers, the molar ratio being x/y=1/9 to 5/5 and (x+y+z)/z=1/0.1 to 1/0.002; and water, wherein the mass ratio of component (A) and component (C), (A)/(C), is =3 to 46.

2. The method according to claim 1, wherein the hair cosmetic further comprises from 0.05 to 2 mass % of component (D) a betaine-based amphoteric surfactant.

3. The method according to claim 2, wherein the component (D) is an alkylhydroxysulfobetaine having an alkyl group having 10 to 16 carbon atoms.

4. The method according to claim 1, wherein the hair cosmetic further comprises component (E) an organic carboxylic acid.

5. The method according to claim 4, wherein component (E) is at least one member selected from the group consisting of malic acid and lactic acid, and wherein the content of the component (E) in the hair cosmetic is from 0.1 to 5 mass %.

6. The method according to claim 1, wherein the hair cosmetic has a pH of 1 to 5 when diluted 20 times by mass with water.

\* \* \* \* \*